US00PP30296P3

(12) United States Plant Patent
Ranney

(10) Patent No.: US PP30,296 P3
(45) Date of Patent: Mar. 19, 2019

(54) ***HYDRANGEA* PLANT NAMED 'NCHA5'**

(50) Latin Name: *Hydrangea arborescens*
Varietal Denomination: NCHA5

(71) Applicant: Thomas Green Ranney, Arden, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/731,346

(22) Filed: May 30, 2017

(65) Prior Publication Data

US 2018/0352699 P1 Dec. 6, 2018

(51) Int. Cl.
*A01H 5/00* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

*Primary Examiner* — Susan McCormick Ewoldt
(74) *Attorney, Agent, or Firm* — Cassandra Bright

(57) ABSTRACT

A new and distinct *Hydrangea* cultivar named 'NCHA5' is disclosed, characterized by large, mop-head inflorescences with white sepals. Plant habit is dwarf and rounded with strong stems. Plants are triploid. The new variety is a *Hydrangea* normally produced as an outdoor garden or container plant.

3 Drawing Sheets

Latin name of the genus and species: *Hydrangea arborescens.*
Variety denomination: 'NCHA5'.

BACKGROUND OF THE INVENTION

The present invention comprises a new and distinct *Hydrangea* cultivar hereinafter referred to by the cultivar name 'NCHA5'. This new *Hydrangea* was developed through a breeding program at North Carolina State University, Mills River, N.C. 'NCHA5' was selected from a population of seedlings that resulted from a cross of *Hydrangea arborescens* 'H2009-068-007' (unpatented pollen parent) and *Hydrangea arborescens* 'H2008-143-001' (unpatented seed parent). See FIG. 1 for a complete pedigree. The first asexual propagation of 'NCHA5' was carried out in July 2012 by rooting stem cuttings at the North Carolina State University, Mountain Horticultural Crops Research Station, Mills River, N.C. and has been asexually reproduced repeatedly by vegetative cuttings over a two year period. 'NCHA5' roots readily from softwood cuttings treated with a basal dip of 2,500-5,000 ppm indole butyric acid (potassium salt) in water. 'NCHA5' has been found to retain its distinctive characteristics through successive asexual propagations.

SUMMARY OF THE INVENTION

The following are the unique combination of characteristics of this new cultivar when grown under standard horticultural practices at Mills River, N.C.

1. Large mop-head inflorescences with white florets.
2. Triploid cytotype.
3. Dwarf, rounded habit with strong stems.

COMPARISON WITH COMMERCIAL CULTIVARS

Table 1 shows distinguishing characteristics between 'NCHA5' and other cultivars of *H. arborescens*. 'NCHA5' has a unique combination of traits including large inflorescenses with white sepals, a dwarf habit, and a triploid cytotype.

'NCHA5' is similar in most horticultural characteristics to the seed parent variety, unpatented. The new variety however differs in the following:

1. 'NCHA5' has white sepals, sepals of the seed parent are light red-purple.

'NCHA5' is similar in most horticultural characteristics to the pollen parent variety, unpatented. The new variety however differs in the following:

1. 'NCHA5' has white sepals, sepals of the 'NCHA3' are red-purple.

*Hydrangea* 'NCHA5' can also be compared to the commercial varieties *Hydrangea* 'NCHA4', USSP 28,280 and 'NCHA3', USPP 28,317 which have the same parents as 'NCHA5', but, reversed as seed and pollen parents. 'NCHA5' differs from 'NCHA4' in the following characteristic:

1. 'NCHA5' has white sepals, sepals of 'NCHA4' are red-purple.

'NCHA5' differs from 'NCHA3' in the following characteristics:

1. 'NCHA5' has white sepals, sepals of 'NCHA3' are dark red-purple.

TABLE 1

Comparison to other cultivars.

| | Taxa | | |
|---|---|---|---|
| Trait | *H. aborescens* 'NCHA1' (U.S. Plant Pat. No. 20,765) | *H. arborescens* '' | *H. arborescens* 'NCHA7' (15/731,344) |

TABLE 1-continued

| Comparison to other cultivars. | | | |
|---|---|---|---|
| Ploidy level (genome size, pg) | Diploid (2.7) | Triploid (3.9) | Triploid (3.9) |
| Growth habit | Rounded | Rounded, dwarf | Rounded |
| Height and width | 100 cm × 100 cm | 35 cm × 55 cm | 80 cm × 80 cm |
| Stem internode length | 5 to 15 cm | Avg. 7 cm (4 to 10.5 cm) | Avg. 6 cm (4 to 7 cm) |
| Flower count | | | |
| Fertile | Approx. 600 | Approx. 450 | Approx. 50 |
| Sterile | Approx. 600 | Approx. 900 | Approx. 200 |
| Corymb diameter | 8-20 cm | Avg. 16 cm | Avg. 14 cm |
| Sepal color | | | |
| Above | Red-Purple (ranges from 68D/C to N66D/N66C) | White (155A) to White (N155D) | Red-Purple (60C) |
| Below | Red-Purple (ranges from 68D/C to N66D/N66C) | White (155A) White (N155D) | Red-Purple (60A) |
| Sepal | | | |
| Length | 0.5-0.7 cm | Avg. 0.5 cm | Avg. 0.8 cm |
| Width | 0.3-0.5 cm | Avg. 0.4 cm | Avg. 0.8 cm |

| | | Taxa | |
|---|---|---|---|
| | Trait | *H. arborescens* 'NCHA8' (15/731,345) | *H. arborescens* 'PIIHA-I' (U.S. Plant Pat. No. 21,227) |
| | Ploidy level (genome size, pg) | Triploid (3.9) | Unknown |
| | Growth habit | Rounded | Upright, spreading |
| | Height and width | 60 cm × 60 cm | 90 cm × 90 cm |
| | Stem internode length | Avg. 7 cm (3 to 10 cm) | About 6 cm |
| | Flower count | | |
| | Fertile | Approx. 500 | Approx. 75 |
| | Sterile | Approx. 300 | Approx. 300 |
| | Corymb diameter | Avg. 14 cm | Avg. 12.5 |
| | Sepal color | | |
| | Above | Yellow-Green (145C) fading to Green-White (157C) | Close to Red-Purple (58A) |
| | Below | Yellow-Green (145D) | Close to Red-Purple (63A) |
| | Sepal | | |
| | Length | Avg. 0.5 cm | 0.7 cm |
| | Width | Avg. 0.3 cm | 0.5 cm |

BRIEF DESCRIPTION OF THE DRAWINGS

This new *Hydrangea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Hydrangea*.

DETAILED BOTANICAL DESCRIPTION

Figure 1:
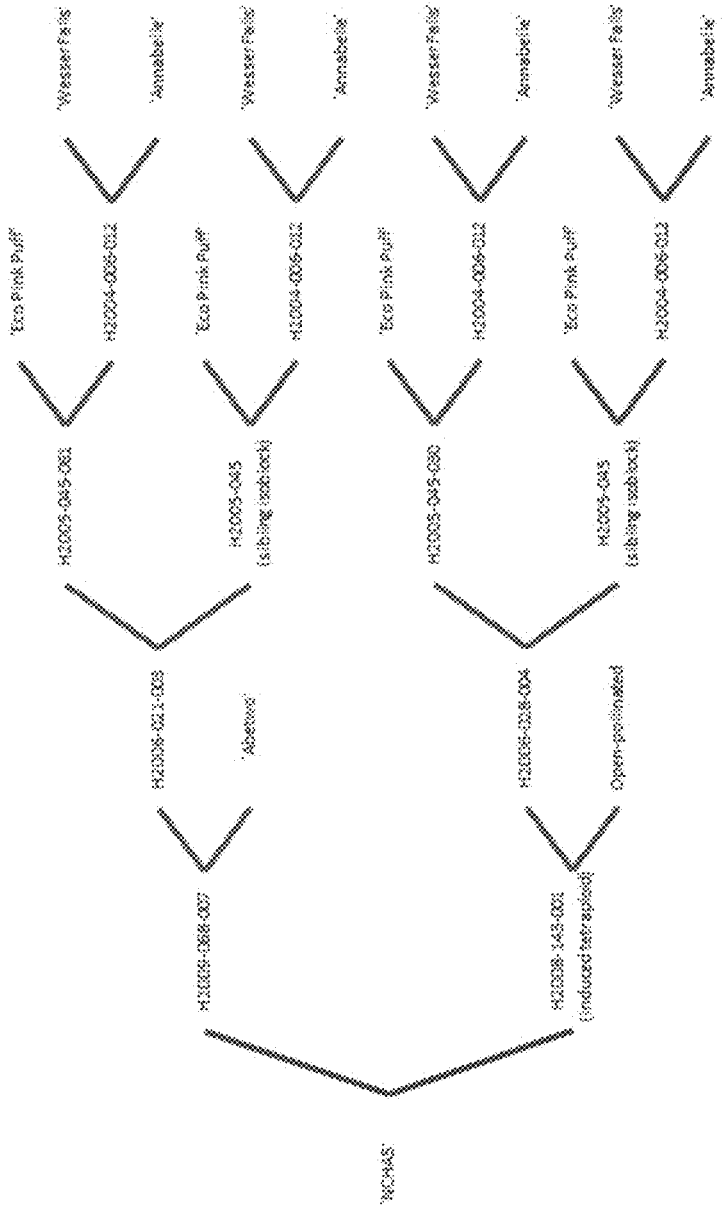
FIG. 1 Shows the pedigree of 'NCHA5'.
Figure 2:
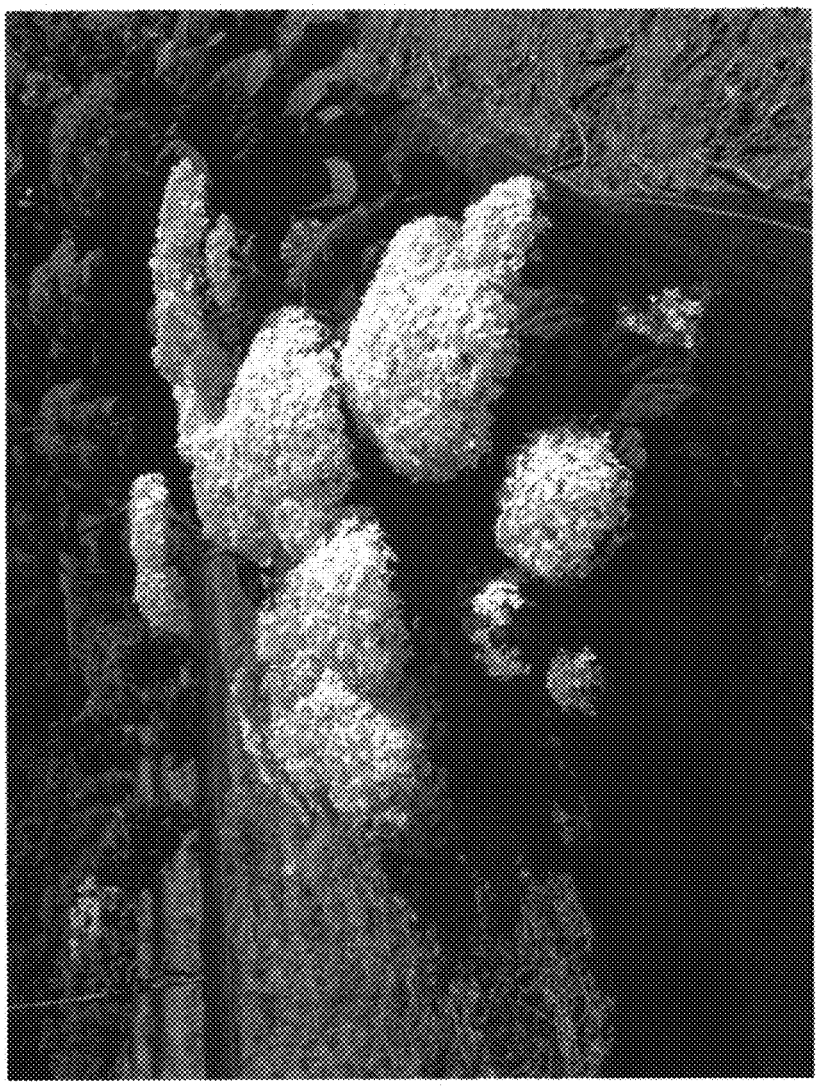
FIG. 2 Shows the inflorescence and plant form of a two-year-old plant of 'NCHA5' growing in Mills River, N.C.
Figure 3:
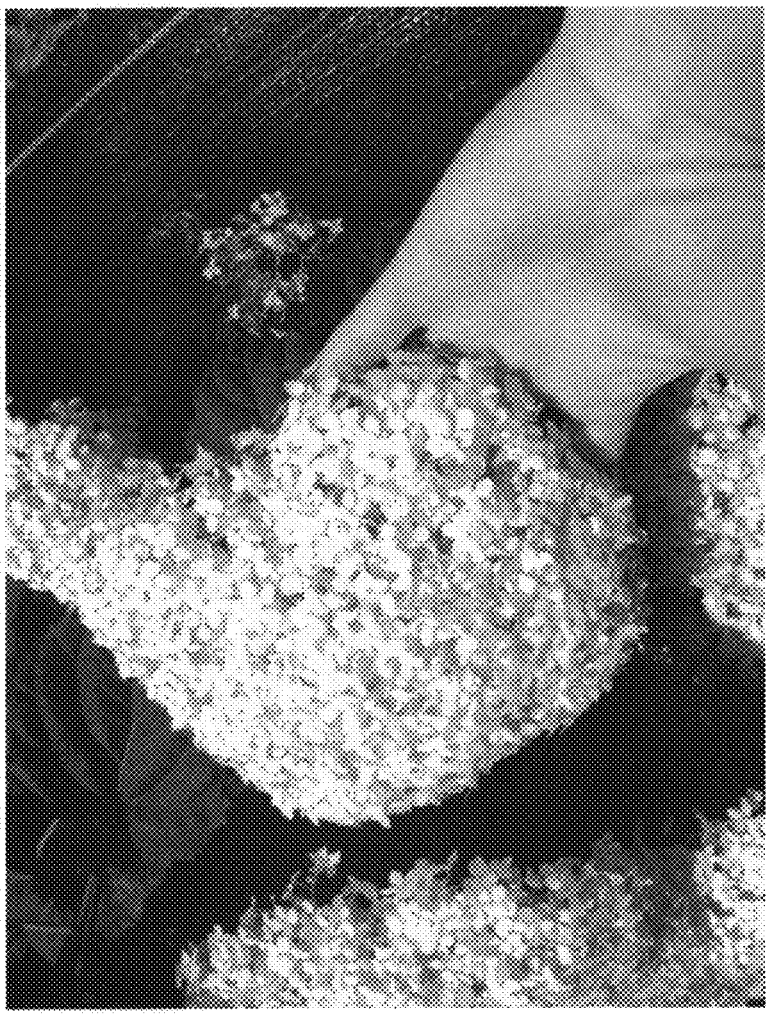
FIG. 3 Shows the white mop-head inflorescence of a two-year-old plant of 'NCHA5' growing in Mills River, N.C.

The following is a detailed description of the botanical characteristics of the new and distinct *Hydrangea* variety plant known by the denomination 'NCHA5'. The detailed description was taken on a two-year-old field-grown plant in Mills River, N.C. in 2016. All colors cited herein refer to The Royal Horticultural Society Colour Chart (The Royal Horticultural Society (R.H.S.), London, Sixth Edition, 2015). Where specific dimensions, sizes, colors, and other characteristics are given, it is to be understood that such characteristics are approximations or averages set forth as accurately as practicable.

Classification:

*Botanical name.*—*Hydrangea arborescens* 'NCHA5'.

*Common name.*—Smooth *Hydrangea.*

Parentage: 'NCHA5' originated as a seedling that resulted from a cross of *H. arborescens* 'H2009-068-007' and *H. arborescens* 'H2008-143-001'.

Plant:

*Growth habit.*—Rounded.

*Height (from top of soil including inflorescences).*—About 35 cm.

*Width (including inflorescences).*—About 55 cm.

*Shoot and stem.*—Length: 30 cm (20 to 35 cm). Diameter: 0.6 cm (0.3 to 0.8 cm). Internode length: 7 cm (4 to 10.5 cm). Immature shoot texture (current year): Pubescent. Immature shoot color (current year): Yellow-Green (146C). Mature stem texture (from prior year): Glabrous, exfoliating. Mature stem color (from prior year): Grey-Brown (199D).

*Branching habit.*—Freely branching with 30-50 shoots.

Foliage:

*Type.*—Simple.

*Persistence.*—Deciduous.

*Arrangement.*—Opposite.

*Shape.*—Broadly ovate.

*Apex.*—Acuminate.

*Base.*—Acute to rounded.

*Venation.*—Pinnate, opposite to subopposite.

*Vein color.*—Upper: Yellow-Green (148B). Lower: Yellow-Green (148D).

*Margins.*—Dentate to serrate.

*Texture.*—Upper surface: Slightly pubescent. Lower surface: Slightly pubescent.

*Emerging leaves.*—Color: Upper and lower: Green (136B).

*Mature leaves during growing season.*—Color: Upper: Green (137A). Lower: Yellow-Green (146A to 146B). Length of lamina: Avg. 8.5 cm (5.5 to 11 cm). Width: Avg. 7.5 cm (4 to 10.5 cm).

*Leaf attachment.*—Petiolate.

*Petiole.*—Length: Avg. 1.5 cm (0.5 to 2 cm). Diameter: Avg. 0.2 cm (0.1 to 0.3 cm). Color: Yellow-Green (146C).

Inflorescence:

*Description*.—Fertile (approximately 450) and sterile (approximately 900) flowers arranged on individual hemispherical or dome-shaped terminal, compound corymbs.

*Flowering season*.—Late May to late June in Mills River, N.C.

*Corymb*.—Diameter: Average 16 cm (12 to 19 cm). Height: Average 8 cm (6 to 10 cm). Quantity: Often 50 corymbs per plant over the flowering season. Longevity: Showy for approximately 4 weeks.

*Sterile flowers*.—Petals, pistils and stamens are greatly reduced (<0.5 mm) and insignificant. Buds: Shape: Oval. Diameter: 0.2 cm. Color: Yellow-Green (148D). Sepals: Number: 2 to 4. Length: Avg. 0.5 cm (0.3 to 0.7 cm). Width: Avg. 0.4 cm (0.3 to 0.5 cm). Shape: Ovate. Apex: Mucronate to rounded. Base: Rounded. Margin: Entire. Texture: Glabrous. Color: Upper: White (155A) to White (N155D). Lower: White (155A) to White (N155D). Sepal overlap: Very slightly at base.

*Fertile flowers*.—Sepals and petals are greatly reduced (<0.5 mm) and insignificant. Buds: Shape: Round. Diameter: 0.2 cm. Color: Yellow-Green (148C). Width: 0.2 cm. Height: 0.2 cm.

Reproductive organs:

*Gynoecium*.—Pistil number: 2, fused. Pistil color: White (155B). Pistil length: 0.1 cm. Stigma shape: Blunt. Stigma diameter: 0.05 cm. Style length: 0.1 cm. Ovary shape: Rounded. Ovary diameter: 0.1 cm.

*Androecium*.—Stamen number: 10. Anther: Shape: Rounded, fusiform. Length: 0.05 cm. Color: White (158D). Filament: Length: 0.1 cm. Color: White (158D). Amount of pollen: None observed.

Other characteristics:

Fruit/seed set: Seeds are minute, dust-like.

Disease and insect resistance: No significant resistance nor susceptibility to disease or insect pests have been observed.

Cold hardiness: At least USDA zone 6b; testing has not been completed in colder zones.

What is claimed is:

1. A new and distinct cultivar of *Hydrangea arborescens* plant named 'NCHA5' as illustrated and described herein.

* * * * *